US012747462B2

(12) United States Patent
Li et al.

(10) Patent No.: US 12,747,462 B2
(45) Date of Patent: Sep. 29, 2026

(54) *BACILLUS LICHENIFORMIS* CELL STABLY AND REPEATEDLY USED FOR CONVERSION AND SYNTHESIS OF D-PSICOSE

(71) Applicant: WUXI INSTITUTE FOR SPECIALIZED NUTRITIONAND HEALTH CO., LTD, Wuxi (CN)

(72) Inventors: Youran Li, Wuxi (CN); Zhiyong Wu, Wuxi (CN); Guiyang Shi, Wuxi (CN)

(73) Assignee: WUXI INSTITUTE FOR SPECIALIZED NUTRITIONAND HEALTH CO., LTD, Wuxi (CN)

( * ) Notice: Subject to any disclaimer, the term of this patent is extended or adjusted under 35 U.S.C. 154(b) by 275 days.

(21) Appl. No.: 18/539,751

(22) Filed: Dec. 14, 2023

(65) Prior Publication Data

US 2024/0117396 A1 Apr. 11, 2024

Related U.S. Application Data

(63) Continuation of application No. PCT/CN2023/118453, filed on Sep. 13, 2023.

(30) Foreign Application Priority Data

Sep. 26, 2022 (CN) ......................... 202211176218.3

(51) Int. Cl.

| | |
|---|---|
| ***C12P 19/02*** | (2006.01) |
| ***C12N 1/02*** | (2006.01) |
| ***C12N 1/205*** | (2026.01) |
| ***C12R 1/10*** | (2006.01) |

(52) U.S. Cl.

CPC ................ *C12P 19/02* (2013.01); *C12N 1/02* (2013.01); *C12N 1/205* (2021.05); *C12R 2001/10* (2021.05)

(58) Field of Classification Search

CPC . C12P 19/02; C12P 19/24; C12N 1/02; C12N 1/205; C12N 9/90; C12N 15/75; C12N 2800/101; C12N 2800/22; C12R 2001/10; Y02P 20/584; C12Y 501/03

See application file for complete search history.

(56) References Cited

U.S. PATENT DOCUMENTS

2018/0112244 A1 4/2018 Venkitasubramanian et al.

FOREIGN PATENT DOCUMENTS

| | | |
|---|---|---|
| CN | 108102995 A | 6/2018 |
| CN | 111032879 A | 4/2020 |
| CN | 112695006 A | 4/2021 |
| CN | 116064619 A | 5/2023 |
| CN | 116676166 A | 9/2023 |

OTHER PUBLICATIONS

Jia, Min et al. "expression of D-Psicose 3-epimerase in Bacillus subtilis" Journal Food and Biotechnology, vol. 33, No. 11, Dec. 31, 2014, p. 1129-1135.

*Primary Examiner* — Ganapathirama Raghu

(74) *Attorney, Agent, or Firm* — IPro, PLLC; Na Xu

(57) ABSTRACT

The present disclosure discloses a *Bacillus licheniformis* cell stably and repeatedly used for the conversion and synthesis of D-psicose, and belongs to the field of biotechnology. D-psicose is a functional sugar with high health value and has broad application prospects in food, medicine, health care and other fields. The *B. licheniformis* cell of the present disclosure efficiently expresses recombinant D-psicose-3-epimerase, and can convert high-concentration fructose as a substrate into D-psicose. After the whole-cell catalyst is reused 10 times, the conversion rate is not less than 30%. Compared with pure enzyme or single-use whole-cell conversion methods, this technology for the synthesis of D-psicose has significant advantages such as low catalyst cost and simple separation and purification.

6 Claims, 4 Drawing Sheets

Specification includes a Sequence Listing.

SEQUENCE LISTING

```
Sequence total quantity: 9
SEQ ID NO: 1           moltype = DNA  length = 882
FEATURE                Location/Qualifiers
source                 1..882
                       mol_type = other DNA
                       organism = synthetic construct
SEQUENCE: 1
atgaaacatg gcatctatta tgcgtattgg gaacaggaat gggaagcgga ttataaatat  60
tatatcgaaa aagtcgcgaa actgggcttt gatatcctgg aaatcgcggc gagcccgctg  120
ccgttttata gcgatatcca gatcaatgaa ctgaaagcgt gcgcgcatgg caacggcatc  180
acgctgacgg tcggccatgg cccgagcgcg gaacagaatc ttagcagccc tgatccggat  240
atccgcaaaa acgcgaaagc gttttatacg gatctgctga aacgcctgta taaactggat  300
gtccatctga tcggcggcgc gctgtatagc tattggccga tcgattatac gaaaacgatc  360
gataaaaaag gcgattggga aagaagcgtc gaaagcgtcc gcgaagtcgc caaagtcgcg  420
gaagcgtgcg gcgtcgattt ttgccttgaa gtcctgaacc gctttgaaaa ctatctgatc  480
aacacggcgc aggaaggagt cgattttgtc aaacaggtcg atcataacaa tgtcaaagtc  540
atgctggata cgtttcatat gaacatcgaa gaagatagca tcggcggcgc gatccgcacg  600
gcgggcagct atcttggcca tctgcatacg ggcgaatgca accgcaaagt tccgggccgc  660
ggccgcatcc cgtgggtcga aatcggcgaa gccctggccg atatcggcta taacggcagc  720
gtcgtcatgg aaccgtttgt cagaatgggc ggcacagtcg gcagcaacat caaagtctgg  780
cgcgatatca gcaacggcgc ggatgaaaaa atgctggatc gcgaagcgca ggcggcgctg  840
gattttagcc gctatgtcct ggaatgccat aaacatagct aa                     882

SEQ ID NO: 2           moltype = DNA  length = 267
FEATURE                Location/Qualifiers
source                 1..267
                       mol_type = other DNA
                       organism = synthetic construct
SEQUENCE: 2
agtttatgta tagatatttt cgaatattta acttattgga cacaataatt ttgaaatagg  60
gcattttgca caagaaataa tccaaaatag cccaaaaata agtttatgta tagatatttt  120
cgaatattta acttattgga cacaataatt ttgaaatagg gcattttgca caagaaataa  180
tccaaaatag cccaaaaata atccaacaat tctaattatt gttataataa tgctgagctc  240
ccaaaattaa ttaagaggtg aaggaaa                                      267

SEQ ID NO: 3           moltype = DNA  length = 133
FEATURE                Location/Qualifiers
source                 1..133
                       mol_type = other DNA
                       organism = synthetic construct
SEQUENCE: 3
caggataagc tccagatcct gctatcaata ccaagtcact gaattacccg tcatgattcc  60
tttcctattg cttgttgtta tgacgggtaa cttctataat taggatttat ttagagtgaa  120
tggtttttta ccc                                                      133

SEQ ID NO: 4           moltype = DNA  length = 1539
FEATURE                Location/Qualifiers
source                 1..1539
                       mol_type = other DNA
                       organism = synthetic construct
```

-continued

```
SEQUENCE: 4
atgaaacaac acaaacggct ttatgcccga ttgctgccgc tgttatttgc gctcatcttc  60
ttgctgcctc actctgcagc agcggcggca agtcttaatg ggacgctgat gcagtatttt  120
gagtggtaca tgccaaatga tggccaacat tggaaacgct tacaaaatga ctcggcatat  180
ttggctgaac acggtattac tgccgtctgg attcccccgg catataaggg aacgagtcaa  240
gacgatgtag gctacggcgc ttacgatctg tatgatttag gggagtttca tcaaaaaggg  300
acggttcgga caaagtacgg cacaaaggga gaactgcaat ctgcgatcaa cagtcttcat  360
tcccgggaca tcaacgttta cggcgatgta gtcatcaacc acaaaggcgg cgctgatgcg  420
accgaatatg taacggctgt tgaagtcgat cccgccgacc gcaaccgcgt aacatcagga  480
gaacagcgaa tcaaagcgtg gacacatttt caattcccgg ggcgcggcag cacatacagc  540
gatttcaaat ggtattggta ccattttgac ggaaccgatt gggacgagtc ccgaaagctg  600
aaccgcatct ataagtttca aggaaaggca tgggattggg aagtttccaa tgaaaacggc  660
aactatgatt acttgatgta tgccgacatc gattatgatc atcctgatgt cacggcagaa  720
ataaagagat ggggaacgtg gtatgccaat gagctgcaat tggacggatt ccgccttgat  780
gccgtcaaac acattaaatt ttcttttttg cgggattggg tcaatcatgt cagggaaaaa  840
acagggaagg aaatgtttac ggtagctgaa tattggcaga atgacttagg tgcgctggaa  900
aactatttga acaaaacaaa ctttaatcat tcagtgtttg acgtgccgct tcattaccag  960
ttccatgctg catcgacaca gggaggcggc tatgatatga ggaaattgct gaacggaaca  1020
gtcgtttcca agcatcctgt gaaagcggtt acgtttgttg ataaccatga tacacagccg  1080
gggcaatcgc ttgagtcgac tgtccaaaca tggtttaagc cgctggctta cgcttttatt  1140
ttgacaagag aagcaggcta cccgcagatt ttctacgggg atatgtacgg gacgaaagga  1200
gcctcgcagc gcgaaattcc tgccctgaaa cacaaaatcg aaccgatctt aaaagcgaga  1260
aaacaatatg cgtacggagc acagcatgat tatttcgatc atcataacat tgtcggctgg  1320
acgagggaag gcgacagctc ggttgcaaat tctggtttgg cggcgttaat aacagacgga  1380
cccggcggga caaagcgaat gtatgtcggc cggcaaaacg ccggtgagac atggcatgac  1440
atcaccggaa accgttccga ttctgttgtc atcaatgcag aaggctgggg agagtttcac  1500
gtaaacggcg gatcggtttc gatctatgtt caaagatag                        1539

SEQ ID NO: 5            moltype = DNA  length = 30
FEATURE                 Location/Qualifiers
source                  1..30
                        mol_type = other DNA
                        organism = synthetic construct
SEQUENCE: 5
gcgcggatcc atgaagcacg gtatctatta                                   30

SEQ ID NO: 6            moltype = DNA  length = 30
FEATURE                 Location/Qualifiers
source                  1..30
                        mol_type = other DNA
                        organism = synthetic construct
SEQUENCE: 6
ccggctagct ggagtgtttg tgacattcta                                   30

SEQ ID NO: 7            moltype = DNA  length = 816
FEATURE                 Location/Qualifiers
source                  1..816
                        mol_type = other DNA
                        organism = synthetic construct
SEQUENCE: 7
atgatgcatt cttgtgtaac tattgcctta gttcctcaaa tcaagtcggg cccctggatt  60
ttttgggaag acttagaagc gagtatggcc caagcgtcta ggctgggatt tgatgccatc  120
gaacttttta cagaagatgc taaaagtctt gataaagggc tattggatgg actattgtca  180
aaatattcat taaaactagc ggcagtggga agtggagctg gaaaagttat tcagggatta  240
acgctgactg accccaatcc agaaatccga acgaaagcta tccattttat tcaatccatg  300
atggattttg gtgcgcattt tggggcggtg accatcattg gttccatgca aggaaatgct  360
ttgcctgatc gtagagagga atctttgatg catttacaag aggccttgga atatctcggg  420
aaacatgcgg agaaactagg agtacctttg atttacgaac ctttgaaccg ttatgaaacc  480
aatttattta ataccttggg ttctggtaaa gcatttgtag aaggtctatc cacgcgtcat  540
atcaaattac tagctgattt gtttcacatg aacatagaag aaatagatat agctcaaagt  600
atcctagaaa atggaccttg gattggtcat gtgcatttag cagattccaa tcgaagaccg  660
atgggaatgg gtcatacttc catgaaagaa atagcagcag ctttacagca aataaattac  720
caaggagcca tatctgcgga agcatttccc tggcctaatc ctttggaagc tgccgagcag  780
accatcaaaa cataccaaca atattttaaa aaataa                            816

SEQ ID NO: 8            moltype = DNA  length = 912
FEATURE                 Location/Qualifiers
source                  1..912
                        mol_type = other DNA
                        organism = synthetic construct
SEQUENCE: 8
atggcattaa acgtaaaatt tggcgtaagc acctggctct ggacgtcccc tttcgattcc  60
actacgctgg cattatttcc caaaattaaa tcgatgggtt acgacgtagt agagattccc  120
gtggaggata ccagtttaat agacgctccc aagttgaaag aagcactgga ggcaaatggt  180
ttggaaggtc taatttgcgg tgcctttggt actacccgcg atttaaccca cgaagacgaa  240
ctctaccaac gtaacagcat cgaatacatt acccaatgtt ttcagatttc cgaagccatt  300
ggttgttctt ttgtatcggg tccgatgtat tcagcggtgg gtaaagccag gttagtttcg  360
ccggaacaaa agaaagttga atgggaccgg gcagttacca acctgcaaaa agtgtgcgct  420
atcgccgacc aatacggcca agccattgcc ttggaaccca tcaatcgttt cgaaaccgat  480
```

-continued

```
ttaataaaca atgccgaaga cgtgatgcag ttaatccgcg acatcaatca tccggctgcc  540
caggtttcgc tggatggttt ccacatgaac attgaagaac cagatatcga gaaagccatt  600
cttttaacgg gcgataaact gcggcacgtg caagtatccg aaaattaccg cggtacgccg  660
ggcaccggcc aaacccgctg ggatgccttt taccgcggct taaccgccat taactaccag  720
ggcgccgttg ccattgaaag tttcaccccc aacgtaaaag aactggccgg agccgtctgc  780
atctggcgcc cactcgccga aagccaggat ggttttgctt cggaaggcat tcaattttta  840
aaaaaatggg ctaaagggga agaaaaggtt aagcaggaag atggtattgc gagtgcttta  900
atagcaaagt ag                                                       912

SEQ ID NO: 9           moltype = DNA  length = 882
FEATURE                Location/Qualifiers
source                 1..882
                       mol_type = other DNA
                       organism = synthetic construct
SEQUENCE: 9
atgaacccga tcggtatgca ctacggtttc tggtctcaca actgggatga aatcgcgtac  60
atcccgctga tggaaaaact ggcatggctg ggttttgata tctgcgaagt tgcgtctgct  120
gaatggggtt attacgatga tgctcgtctg cgtgaactga aagcttgcgc tgatcataat  180
ggtctgggta ttacctactc tattggcctg gaagcgaaat atgatctggc gtctgatgat  240
ccggctgttc gtgaaaacgg catccgtcac gttacccgta ttctggaatc tatgccaaaa  300
gttggtgcag ctattctgaa cggcgtgtct tacgcgggtt ggcaggcgtt accggatcac  360
ggcatcaccc tggatgaaaa acgtcgtaaa gaagaactgg cgctggaatc tatgagccgt  420
ctgatgaaag ttgctgaaga ttgcggtgtt ctgtattgtt gtgaagttgt gaaccgtttt  480
gaacagtatt tactgaacac cgctaaagaa ggtgttgaat tcgttaaacg tctgggtagc  540
ccgaacgctc gtgttctgct ggataccttc cacatgaaca tcgaagaaga ttctatggtt  600
gatgctattt tagaagcggg cccgtggctg ggtcatttcc atgttggtga aaacaaccgt  660
cgtccggcgg gtagcaccaa ccgtctgccg tggaaagata tggcggcggc tctgaaacag  720
gttaactacc agggtgcgat tgttatggaa ccgttcgttc tgatgggtgg caccattccg  780
tatgatatca aagtttggcg tgatctgtct ggtggtgcgg gtgaagcggg cctggatgaa  840
atggcgggtc gtgcgtgtcg ttttctgaaa gaactgaccg cg                      882
```

*BACILLUS LICHENIFORMIS* CELL STABLY AND REPEATEDLY USED FOR CONVERSION AND SYNTHESIS OF D-PSICOSE

REFERENCE TO SEQUENCE LISTING

The instant application contains a Sequence Listing in XML format as a file named "YGHY-2023-03-SEQ.xml", created on Nov. 30, 2023, of 14.1 kB in size, and which is hereby incorporated by reference in its entirety.

TECHNICAL FIELD

The present disclosure relates to a *Bacillus licheniformis* cell stably and repeatedly used for the conversion and synthesis of D-psicose, and belongs to the field of biotechnology.

BACKGROUND

D-psicose is a sugar existed in nature but in very small amounts. It has a sweetness reaching 70% of sucrose, and has a refreshing taste without bitterness. Furthermore, D-psicose cannot be metabolized or is rarely metabolized in the human body. It is evaluated as the most potential sucrose substitute and has broad application prospects in food, medicine, health care and other fields.

The synthesis of D-psicose through chemical routes is difficult and inefficient. The bioconversion method has the advantages of mild reaction conditions, few by-products, simple purification steps, and environmental friendliness, and has gradually become the main direction for the synthesis of D-psicose. At present, the bioconversion of D-psicose mainly relies on the expression of D-psicose-3-epimerase in hosts such as *Escherichia coli, Corynebacterium glutamicum*, or *Bacillus subtilis*, then the acquisition of pure enzyme through cell disruption, and the conversion and synthesis of D-psicose using D-fructose as the substrate. In such production method, the pure enzyme as a catalyst can only be used once and brings challenges to the isolation of the product. At present, there are relatively few reports on the use of whole-cell conversion to synthesize D-psicose, and the main host cells used are *E. coli, C. glutamicum*, or *B. subtilis*. The whole-cell catalysis eliminates the need for cell disruption after fermentation, and the catalyst can be easily separated from the product by centrifugation or filtration. However, cells of *E. coli, C. glutamicum* or *B. subtilis* are easily lysed at a catalytic temperature of 60-70 °C; and even if the cells are recovered, they are easily infected with phages during the process. According to literature reports, *B. subtilis* suffers from severe autolysis phenomenon. As noted in "However, there is a problem with cell autolysis in fermentation cultures of *B. subtilis*." "As mentioned in the article by Regamey and Karamat et al., after *B. subtilis* was subjected to thermal excitation at 50° C, prophage sp6 was induced, and many cells underwent autolysis.", and also as pointed out in the paper Ren, K.; Wang, Q.; Hu, M.; Chen, Y.; Xing, R.; You, J.; Xu, M.; Zhang, X.; Rao, Z. Research Progress on the Effect of Autolysis to *Bacillus subtilis* Fermentation Bioprocess. Fermentation 2022, 8, 685., *B. subtilis* has the problem of autolysis, and especially in high temperature environment (50 °C), the autolysis is more severe. Therefore, it is difficult to reuse whole-cell catalysts.

*B. licheniformis* is widely used as a production host for food enzyme preparations and important nutritional chemicals. Its products are certified by the FDA as "generally regarded as safe" (GRAS) safety level. On the other hand, this strain is a typical heat-resistant microorganism that can grow at 50 °C. The cultured cells have excellent stability at 60-70 °C, and there are few problems with phage infection. The engineered bacteria constructed using *B. licheniformis* can be stably and repeatedly used for the conversion and synthesis of D-psicose, which has obvious advantages over existing methods in terms of production efficiency and cost.

SUMMARY

The first objective of the present disclosure is to provide a gene encoding D-psicose-3-epimerase with a nucleotide sequence shown as SEQ ID NO. 1.

The second objective of the present disclosure is to provide a vector for expressing the above gene.

In one embodiment, the vector is pHY300-PLK.

The third objective of the present disclosure is to provide a cell carrying the above gene or the above vector.

In one embodiment, the cell is *B. licheniformis*.

In one embodiment, the *B. licheniformis* includes *B. licheniformis* CICIM B1341.

The fourth objective of the present disclosure is to provide recombinant *B. licheniformis* carrying the above gene encoding D-psicose-3-epimerase.

In one embodiment, the gene of D-psicose-3-epimerase is initially expressed from promoter $P_{Ian}$.

In one embodiment, the gene of D-psicose-3-epimerase is integrated into a site of amylase encoding gene amyL in a *B. licheniformis* genome.

In one embodiment, a nucleotide sequence of the promoter $P_{Ian}$ is shown in SEQ ID NO. 2.

In one embodiment, a nucleotide sequence of the amylase encoding gene is shown in SEQ ID NO. 4.

In one embodiment, an expression vector of the recombinant *B. licheniformis* is pHY300-PLK.

In one embodiment, the recombinant *B. licheniformis* uses *B. licheniformis* CICIM B1341 as a host.

In one embodiment, the *B. licheniformis* CICIM B1341 is derived from a natural strain preserved in China University Industrial Microbiology Resource Platform.

The fifth objective of the present disclosure is to provide a whole-cell catalyst, which includes the above recombinant *B. licheniformis*.

The sixth objective of the present disclosure is to provide a method for constructing the recombinant *B. licheniformis*, including fusing the D-psicose-3-epimerase gene a1 with the promoter $P_{Ian}$ and terminator ter to obtain an integrated fragment, after connecting the integrated fragment to the pHY300-PLK vector, obtaining recombinant plasmid pHY300-PIan-a1, transferring the recombinant plasmid into *B. licheniformis*, and integrating expression cassettes of the D-psicose-3-epimerase gene into the site of the amylase encoding gene amyL in the *B. licheniformis* genome through subculture.

In one embodiment, the nucleotide sequence of the promoter $P_{Ian}$ is shown in SEQ ID NO. 2, and the nucleotide sequence of the terminator ter is shown in SEQ ID NO. 3.

In one embodiment, the nucleotide sequence of the amylase encoding gene is shown in SEQ ID NO. 4.

The seventh objective of the present disclosure is to provide a method for synthesis of D-psicose through whole-cell conversion, including using D-fructose as a substrate, and adding the recombinant *B. licheniformis* or wet cells of the whole-cell catalyst, reacting at 50-70 °C for 5-10 h.

In one embodiment, after the reaction is completed, the recombinant *B. licheniformis* or the whole-cell catalyst is recovered, reused, and added to a reaction system using the D-fructose as the substrate to synthesize D-psicose.

In one embodiment, the number of repeated uses is more than 10 times.

In one embodiment, the recombinant *B. licheniformis* or the whole-cell catalyst is inoculated into a seed medium and cultured at 37 °C to 42 °C for 12-24 h, then transferred to a fermentation medium at an inoculation amount of 1% to 5% by volume, and cultured at 37 °C to 42 °C for 24-36 h, and wet cells are collected.

In one embodiment, an $OD_{600}$ value of the wet cells is 50 to 100.

In one embodiment, the seed medium includes tryptone 8-12 g/L, yeast powder 4-6 g/L, and NaCl 8-12 g/L.

In one embodiment, the fermentation medium includes (g/L): 20-70 of sucrose, 10-30 of cottonseed protein, 9.12 of $K_2HPO_4{\cdot}3H_2O$, 1.36 of $KH_2PO_4$, 10 of $(NH_4)_2HPO_4$; and initial pH is 7.5.

The present disclosure also provides application of the above gene, or the above vector, or the above cell, or the above recombinant *B. licheniformis*, or the application of the above whole-cell catalyst in the preparation of products containing D-psicose.

Compared with the related art, the positive progressive effects of the present disclosure are as follows:

1. The present disclosure uses the food-safe microorganism *B. licheniformis* as a starting strain, and utilizes its cell's good tolerance to high temperatures to protect the D-psicose-3-epimerase expressed in the cell during the catalytic process. The recombinant *B. licheniformis* provided by the present disclosure can proliferate at 37-42 °C.
2. The present disclosure constructs the gene encoding D-psicose-3-epimerase with a nucleotide sequence as shown in SEQ ID NO. 1 into *B. licheniformis* to obtain the whole-cell catalyst. The whole-cell catalyst can repeat the fermentation reaction 10 times at a temperature of 60 °C, and the conversion rate is not less than 30%. Compared with other pure enzyme conversion methods that use one-time catalysts or whole-cell catalysis methods that are prone to cell rupture, the technical solution of the present disclosure has significant advantages in terms of production cost and efficiency.

DETAILED DESCRIPTION

Figure 1:
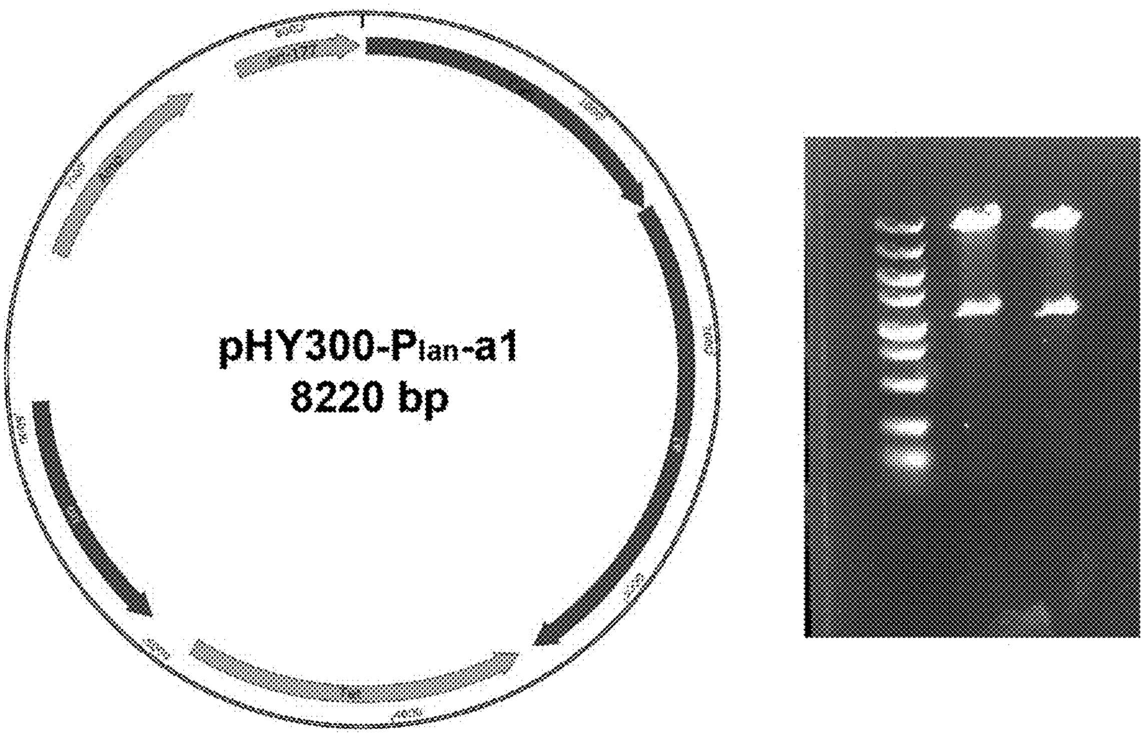
FIG. 1: Map and enzyme digestion verification of recombinant plasmid pHY300-$P_{Ian}$-a1.

The present disclosure will be further described below with reference to the accompanying drawings and specific examples, but the examples do not limit the present disclosure in any form. Unless otherwise stated, the reagents and materials used in the following examples are commercially available or can be prepared by known methods.

Methods Involved in the Following Examples:

1. Determination method for D-psicose: A catalytic reaction system is centrifuged at 13000 r/min for 20 min. A supernatant is diluted 2 times with anhydrous ethanol, left to stand at 4 °C for 2 h, and then filtered with a 0.22 μM water membrane. D-psicose is detected by high performance liquid chromatography.

HPLC detection conditions: 250 mm*4.6 μm Polyamino HILIC column is used, a mobile phase is acetonitrile: water=75:25, a detector is a differential detector, a flow rate is 1 mL/min, a column temperature is 40 °C, and a differential detector cell temperature is 40 °C.

2. Enzyme activity determination method for D-psicose-3-epimerase: 1 mL of fermentation broth sample is taken, and centrifuged at 12000 r/min for 5 min. A precipitate is repeatedly washed and blown with phosphate buffer (50 mmol/L, pH 7.5), and centrifuged three times. The bacterial precipitate is diluted to an appropriate concentration, and resuspended with a fructose substrate solution prepared with HEPEs buffer (50 mmol/L, pH 7.5) to a final volume of 1 mL (fructose mass concentration of 90 g/L, and $Co^{2+}$ and $Mn^{2+}$ concentration of 1 mmol/L). After incubation at 60 °C for 10 min and boiling to inactivate enzyme for 5 min, the resulting solution is centrifuged at 12000 r/min for 5 min. A supernatant is filtered through a 0.22 μm filter, and D-psicose is analyzed using HPLC conditions.

Definition of enzyme activity: the enzyme activity that converts fructose into 1 mg D-psicose within 1 h, which is defined as 1 U.

Plasmids and Strains Involved in the Following Examples:

*B. licheniformis*: CICIM B1341, preserved in this laboratory, can be purchased from the China University Industrial Microbiology Resource and Information Center of Jiangnan University.

Media Involved in the Following Examples:

Seed medium (g/L): 10 of tryptone, 5 of yeast powder, and 10 of NaCl.

Fermentation medium (g/L): 70 of sucrose, 30 of cottonseed protein, 9.12 of $K_2HPO_4{\cdot}3H_2O$ 9.12, 1.36 of $KH_2PO_4$ 1.36, 10 of $(NH_4)_2HPO_4$ 10; and initial is pH 7.5.

Example 1: Construction of a Recombinant *B. licheniformis* Strain Overexpressing D-psicose-3-epimerase Gene (1) Knockout of Amylase Encoding Gene amyL and Integrative Expression of D-Psicose-3-Epimerase Gene Using a codon-optimized a1 gene fragment expression cassette fused with promoter and terminator as a template, the gene was amplified to obtain an expression cassette containing the a1 gene fragment with a nucleotide sequence as shown in SEQ ID NO. 1. Amplification primers were as follows:

```
Upstream primer:
                                          SEQ ID NO. 5
5-GCGCGGATCCATGAAGCACGGTATCTATTA-3 (BamHI),;

Downstream primer:
                                          SEQ ID NO. 6
5-CCGGAAGCTTGGAGTGTTTGTGACATTCTA-3 (HindIII),;
```

and

PCR conditions: denaturation at 94 °C for 2 min, denaturation at 98 °C for 30 s, annealing at 50 °C for 30 s, and extension at 68 °C for 1 min.

A pHY300-PLK vector (from the same source as Li, Y.; Jin, K.; Zhang, L.; Ding, Z.; Gu, Z.; Shi, G. Development of an Inducible Secretory Expression System in *Bacillus licheniformis* Based on an Engineered Xylose Operon. *Journal of Agricultural and Food Chemistry* 2018, 66, 9456-9464.) and the expression cassette containing the a1 gene fragment obtained by PCR amplification were digested with two restriction enzymes, BamHI and HindIII at 37 ° C, and ligated with T4 ligase at 16 °C. The resulting ligation product was transformed into *E. coli* DH5a and screened using Ampicillin-resistant seed medium plates. Transformants were selected for plasmid extraction, enzyme digestion verification, and gene sequencing. Recombinant plasmid with correct sequencing was named pHY300-$P_{Ian}$-a1, as shown in FIG. 1.

The recombinant plasmid pHY300-$P_{Ian}$-a1 was extracted from *E. coli*, with addition of the homology arm of the amylase encoding gene amyL according to a method in Li, Y.; Jin, K.; Zhang, L.; Ding, Z.; Gu, Z.; Shi, G. Development of an Inducible Secretory Expression System in *Bacillus licheniformis* Based on an Engineered Xylose Operon. *Journal of Agricultural and Food Chemistry* 2018, 66, 9456-9464., and then introduced into *B. licheniformis* to obtain recombinant *B. licheniformis* BLA1 with integration of the a1 gene fragment expression cassette at a site of the amylase encoding gene amyL.

(2) Free Expression of D-Psicose-3-Epimerase Gene

Using a codon-optimized a1 gene fragment expression cassette fused with promoter and terminator as a template, the gene was amplified to obtain an expression cassette containing the a1 gene fragment with a nucleotide sequence as shown in SEQ ID NO. 1. Amplification primers were as follows:

```
Upstream primer:
                                          SEQ ID NO. 5
5-GCGCGGATCCATGAAGCACGGTATCTATTA-3 (BamHI),;

Downstream primer:
                                          SEQ ID NO. 6
5-CCGGAAGCTTGGAGTGTTTGTGACATTCTA-3 (HindIII),;
```

and

PCR conditions: denaturation at 94 °C for 2 min, denaturation at 98 °C for 30 s, annealing at 50 °C for 30 s, and extension at 68 °C for 1 min.

Figure 2:
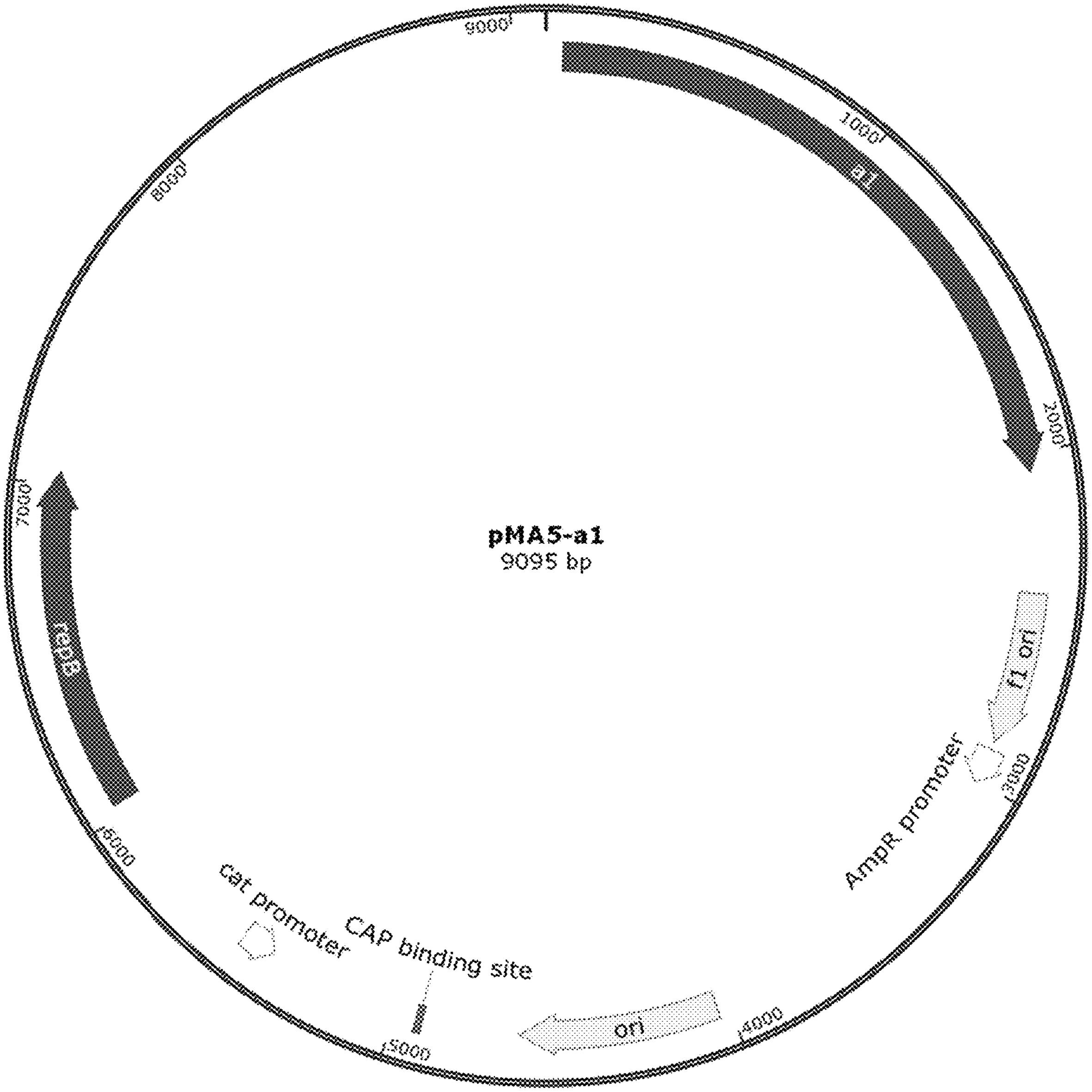
FIG. 2: Map of recombinant plasmid pMA5-a1.

A pMA5 vector (from Xu, Yinbiao, et al. "Unraveling the specific regulation of the shikimate pathway for tyrosine accumulation in *Bacillus licheniformis*." *Journal of Industrial Microbiology and Biotechnology* 46.8 (2019): 1047-1059.) and the expression cassette containing the a1 gene fragment obtained by PCR amplification were digested with two restriction enzymes, BamHI and HindIII at 37 °C, and ligated with T4 ligase at 16 °C. The resulting ligation product was transformed into *E. coli* DH5a and screened using Ampicillin-resistant seed medium plates. Transformants were selected for plasmid extraction, enzyme digestion verification, and gene sequencing. Recombinant plasmid with correct sequencing was named pMA5-a1, as shown in FIG. 2.

The recombinant plasmid pMA5-a1 was extracted from *E. coli*, and according to a method in Li, Y.; Jin, K.; Zhang, L.; Ding, Z.; Gu, Z.; Shi, G. Development of an Inducible Secretory Expression System in *Bacillus licheniformis* Based on an Engineered Xylose Operon. *Journal of Agricultural and Food Chemistry* 2018, 66, 9456-9464., introduced into *B. licheniformis* to obtain recombinant *B. licheniformis* BLA2 with free expression of the a1 gene fragment expression cassette.

(3) Knockout of Amylase Encoding Gene aprE and Integrative Expression of D-Psicose-3-Epimerase Gene Using a codon-optimized a1 gene fragment expression cassette fused with promoter and terminator as a template, the gene was amplified to obtain an expression cassette containing the a1 gene fragment with a nucleotide sequence as shown in SEQ ID NO. 1. Amplification primers were as follows:

```
Upstream primer:
                                          SEQ ID NO. 5
5-GCGCGGATCCATGAAGCACGGTATCTATTA-3 (BamHI),;

Downstream primer:
                                          SEQ ID NO. 6
5-CCGGAAGCTTGGAGTGTTTGTGACATTCTA-3 (HindIII),;
```

and

PCR conditions: denaturation at 94 °C for 2 min, denaturation at 98 °C for 30 s, annealing at 50 °C for 30 s, and extension at 68 °C for 1 min.

A pHY300-PLK vector (from the same source as Li, Y.; Jin, K.; Zhang, L.; Ding, Z.; Gu, Z.; Shi, G. Development of an Inducible Secretory Expression System in *Bacillus licheniformis* Based on an Engineered Xylose Operon. *Journal of Agricultural and Food Chemistry* 2018, 66, 9456-9464.) and the expression cassette containing the a1 gene fragment obtained by PCR amplification were digested with two restriction enzymes, BamHI and HindIII at 37 °C, and ligated with T4 ligase at 16 °C. The resulting ligation product was transformed into *E. coli* DH5a and screened using Ampicillin-resistant seed medium plates. Transformants were selected for plasmid extraction, enzyme digestion verification, and gene sequencing. Recombinant plasmid with correct sequencing was named pHY300-$P_{Ian}$-a1, as shown in FIG. 1.

The recombinant plasmid pHY300-$P_{Ian}$-a1 was extracted from *E. coli*, with addition of the homology arm of the amylase encoding gene aprE according to a method in Li, Y.; Jin, K.; Zhang, L.; Ding, Z.; Gu, Z.; Shi, G. Development of an Inducible Secretory Expression System in *Bacillus licheniformis* Based on an Engineered Xylose Operon. *Journal of Agricultural and Food Chemistry* 2018, 66, 9456-9464., and then introduced into *B. licheniformis* to obtain recombinant *B. licheniformis* BLA3 with integration of the a1 gene fragment expression cassette at a site of the amylase encoding gene aprE.

Example 2: Culture and Enzyme Production of Different Recombinant Bacterial Cells The recombinant *B. licheniformis* BLA1, BLA2 and BLA3 constructed in Example 1 were respectively inoculated into fermentation media and cultured at 37 °C. Samples were taken at 72 h to detect the cell OD 600 and product concentration. Table 1 showed OD 600 values and enzyme activity yields of the cells after fermentation culture of different recombinant bacteria. The results showed that the enzyme activity of integrative expression of the D-psicose-3-epimerase gene into the site of the amylase encoding gene amyL was significantly higher than the enzyme activity of free expression or integrative expression into the site of the amylase encoding gene aprE.

TABLE 1

Cell concentration and enzyme activity of recombinant bacteria at different temperatures

| | $OD_{600}$ | Enzyme activity (U/mL) |
|---|---|---|
| BLA1 | 31.44 | 106.25 |
| BLA2 | 28.21 | 59.30 |
| BLA3 | 33.83 | 52.65 |

Example 3: Culture and Enzyme Production of Recombinant Bacterial Cells BLA1 at Different Temperatures The recombinant *B. licheniformis* BLA1 constructed in Example 1 was inoculated into a fermentation medium and cultured at 37 °C and 42 °C respectively. On the third and fourth days, samples were taken to detect the cell OD 600 and product concentration. Table 2 showed $OD_{600}$ values of bacterial cells at 37 °C and 42 °C. The number of cells was higher at 37 ° C after 72 h of fermentation culture, and the number of cells was higher at 42 °C after 96 h of fermentation culture. At the same temperature, the number of bacterial cells on the fourth day was higher than that on the third day, indicating that the growth trends of the two were the same, but the growth rate of cell mass was different. The growth rate of cell mass was higher at 42 °C. The enzyme activity was higher at 37 °C after 72 h of fermentation culture.

TABLE 2

Cell concentration and enzyme activity of recombinant bacteria at different temperatures

| | $OD_{600}$ at 37° C. | $OD_{600}$ at 42° C. | Enzyme activity at 37° C. (U/mL) | Enzyme activity at 42° C. (U/mL) |
|---|---|---|---|---|
| 72 h | 31.44 | 20.48 | 106.25 | 45.00 |
| 96 h | 40.10 | 54.00 | 77.75 | 44.75 |

Figure 3:
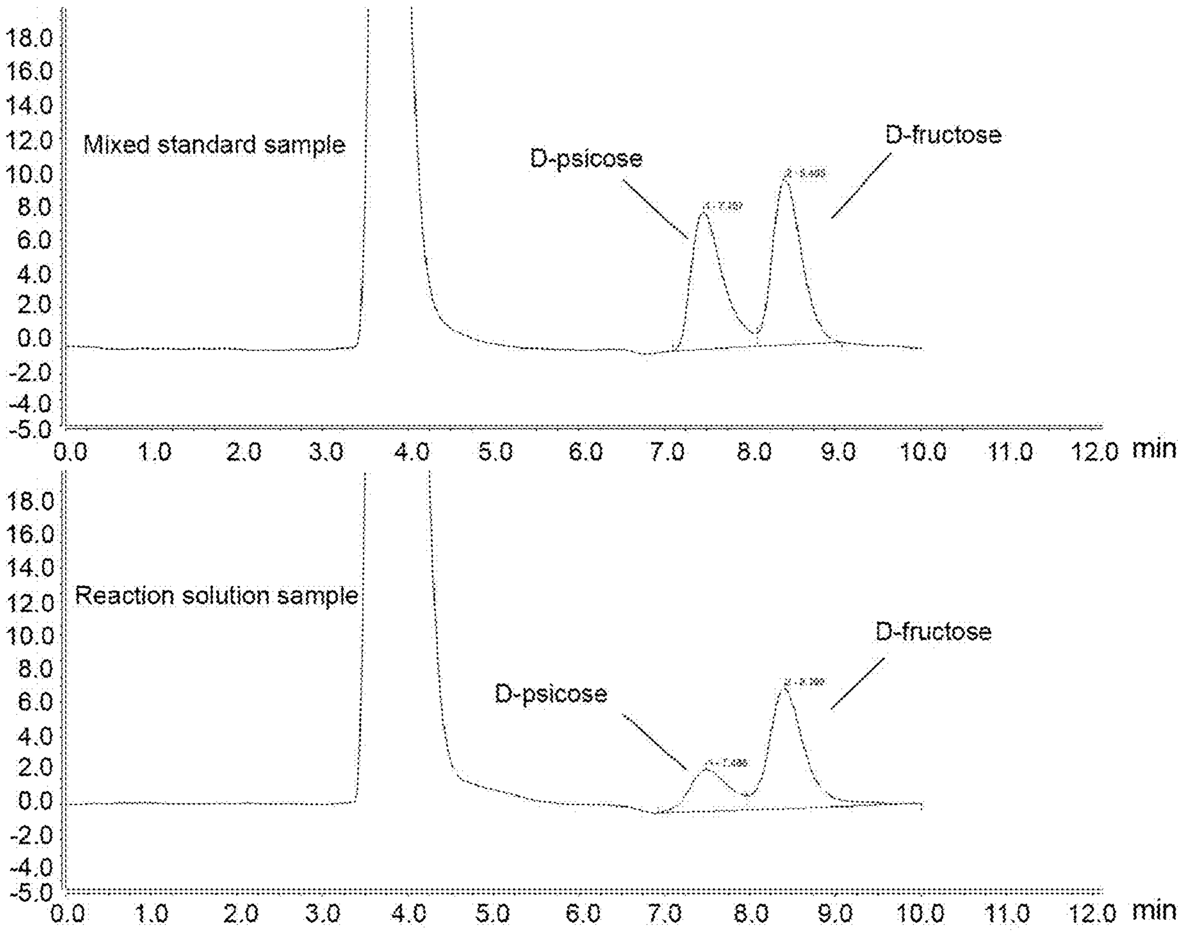
FIG. 3: HPLC spectrum of a reaction solution.

Example 4: Reusable Whole-Cell Conversion (1) Cell Filtration Through Centrifugation The recombinant *B. licheniformis* BLA1 constructed in Example 1 was inoculated into a seed medium and cultured at 37 °C for 12-24 h, and then transferred to a fermentation medium at an inoculation amount of 1% to 5% (v/v) and cultured at 37 °C for 24-36 h. 1 mL of fermentation broth was taken, the cell $OD_{600}$ value was measured using 100 µl of the broth, and the remaining fermentation broth was centrifuged at 12000 r/min and 4 °C for 20 min. A supernatant was discarded, and a precipitate was washed once with 10 mM PB buffer. Centrifugation was carried out again. A supernatant was discarded, and a corresponding volume of PB buffer was added to resuspend a precipitate so as to achieve the cell OD 600 value of 80. An appropriate amount of cell suspension was taken and added to 500 mM HEPEs buffer with pH 7.5 (containing 5 mM $CoCl_2$ and 5 mM $MnCl_2$) and an equal volume of 400 g/L (initial concentration) fructose solution, where the volume ratio of fructose solution and HEPEs buffer was 10:3, and the reaction was carried out in a metal bath at 60 °C for 6 h. After the reaction is completed, the mixture was centrifuged at 12,000 r/min for 20 min, and a precipitate was used for the reuse of the whole-cell catalyst. A supernatant was mixed with an equal volume of anhydrous ethanol, left to stand at 4 °C for 2 h or more, and centrifuged at 12,000 r/min for 20 min. A supernatant was taken and diluted 50 times, filtered through a water-based filter head to 200 µL in a lined tube, and placed in a liquid phase detection bottle for liquid phase detection. The results were shown in FIG. 3: There was an analytical peak of D-psicose in the reaction solution, the yield of D-psicose was 124.4 g/L, and the conversion rate was 31.4%.

Figure 4:
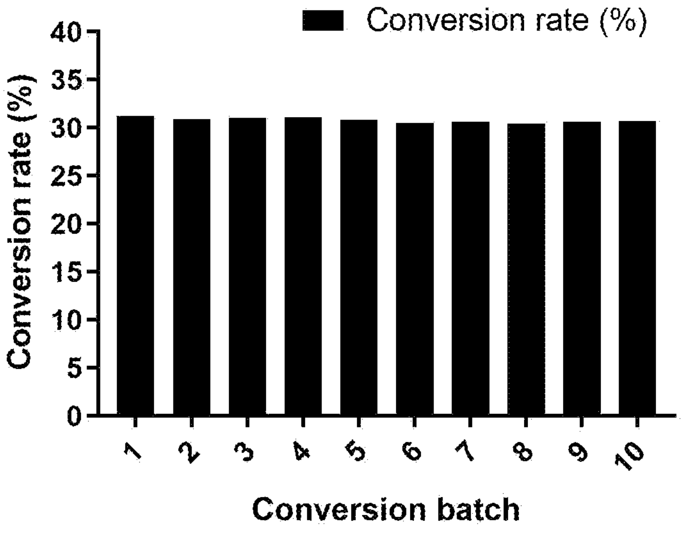
FIG. 4: Reusing 10 batches of whole-cell catalytic synthesis of D-psicose.

The same batch of whole-cell catalyst was reused 10 times. The results showed that after the whole-cell catalyst was reused 10 times, the conversion rate was no less than 30% (FIG. 4).

(2) Cell Filtration Through Microfiltration

Figure 5:
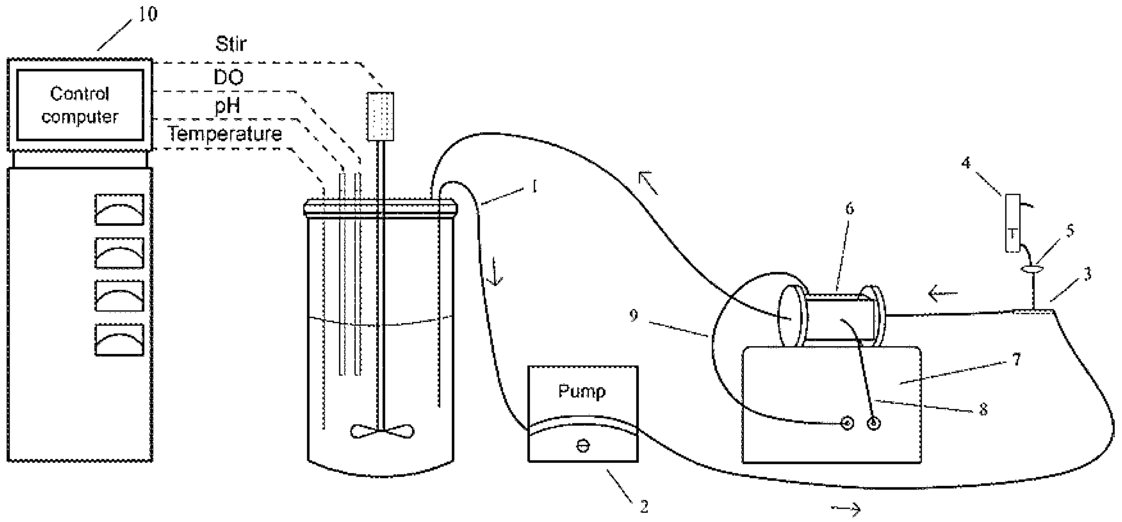
FIG. 5: Single ceramic membrane continuous bioconversion device. 1—Sampling tube, 2—Peristaltic pump, 3—Three-way glass tube, 4—Air flowmeter, 5—Sterile air filter membrane, 6—Flow cell, 7—Near-infrared spectrometer, 8, 9—Optical fiber probes, 10—Fermentation control computer.

To achieve continuous production of D-psicose using *B. licheniformis*, a small-scale continuous bioconversion device was assembled through coupling ceramic membranes, pumps, constant temperature water baths, reactors and other equipment (FIG. 5), aiming to simulate industrial production. The selection of the circulation unit was based on industrial production applications. The pressure on cells during the production and preparation process was greater than or equal to the industrial production level.

The stability and catalytic activity of bacterial cells for continuous D-psicose production were tested through ceramic membrane microfiltration cycles. A total of 10 microfiltrations were completed.

TABLE 3

Cell stability test and continuous microfiltration data

| Sample No. | $OD_{600}$ | Unit cell enzyme activity $U/OD_{600}$ | Flow rate (L/h) | Membrane filtration pressure ($kg/cm^2$) | Microfiltration time (min) |
|---|---|---|---|---|---|
| F0 | 3.0 | — | 150 | 0.9 | — |
| F1 | 3.0 | 3.4 | 150 | 0.9 | 33 |
| F2 | 3.0 | 3.4 | 150 | 0.9 | 50 |
| F3 | 3.0 | 3.4 | 150 | 0.9 | 53 |
| F4 | 3.0 | 3.3 | 150 | 0.9 | 57 |
| F5) | 3.0 | 3.3 | 150 | 0.9 | 67 |
| F6 | 2.9 | 3.3 | 150 | 0.9 | 65 |
| F7 | 2.9 | 3.3 | 150 | 0.9 | 62 |
| F8 | 2.9 | 3.3 | 150 | 0.9 | 62 |
| F9 | 2.9 | 3.3 | 150 | 0.9 | 62 |
| F10 | 2.9 | 3.3 | 150 | 0.9 | 62 |

The results showed that the recombinant *B. licheniformis* BLA1 constructed in Example 1 had high cell stability and low lysis degree during the cycle catalysis process of the reaction device. After 10 cycles, the cell retention rate was 96.7%, and the enzyme activity retention rate per unit cell was 97%, indicating the potential for industrial-scale production.

Comparative Example 1

The gene encoding D-psicose-3-epimerase with the nucleotide sequence shown in SEQ ID NO. 7 was constructed into *B. licheniformis* using the same method as in Example 1 to obtain recombinant *B. licheniformis* BLA7, and D-psicose was produced using the whole-cell conversion method in Example 3. The results showed that at the same concentration, the conversion rate of recombinant *B. licheniformis* BLA7 was only 13.2%, and the conversion rate of recombinant *B. licheniformis* BLA1 was 2.3 times higher.

Comparative Example 2

The gene encoding D-psicose-3-epimerase with the nucleotide sequence shown in SEQ ID NO. 8 was constructed into *B. licheniformis* using the same method as in Example 1 to obtain recombinant *B. licheniformis* BLA8, and D-psicose was produced using the whole-cell conversion method in Example 3. The results showed that at the same concentration, the conversion rate of recombinant *B. licheniformis* BLA8 was only 11.7%, and the conversion rate of recombinant *B. licheniformis* BLA1 was 2.6 times higher.

Comparative Example 3

The gene encoding D-psicose-3-epimerase with the nucleotide sequence shown in SEQ ID NO. 9 was constructed into *B. licheniformis* using the same method as in Example 1 to obtain recombinant *B. licheniformis* BLAS, and D-psicose was produced using the whole-cell conversion method in Example 3. The results showed that at the same concentration, the conversion rate of recombinant *B. licheniformis* BLAS was only 8.3%, and the conversion rate of recombinant *B. licheniformis* BLA1 was 3.7 times higher.

Although the present disclosure has been disclosed with the above exemplary examples, it is not intended to limit the present disclosure. Any person skilled in the art can make various changes and modifications without departing from the spirit and scope of the present disclosure, so the scope of protection of the present disclosure shall be subject to the scope defined by the claims.

What is claimed is:

1. A recombinant *Bacillus licheniformis*, wherein the *B. licheniformis* is *B. licheniformis* CICIM B1341 and was deposited at Guangdong Microbiological Culture Collection Center (GDMCC) on Dec. 8, 2023, with the preservation number of GDMCC NO: 64126, and wherein the *B. licheniformis* CICIM B1341 comprises the gene set forth in SEQ ID NO: 1.

2. The recombinant *B. licheniformis* according to claim 1, wherein the gene is under control of an expression vector pHY300.

3. The recombinant *B. licheniformis* according to claim 1, wherein the gene is integrated into a site of amylase encoding gene amyL in the *B. licheniformis* genome.

4. A whole-cell catalyst, comprising the recombinant *B. licheniformis* of claim 1.

5. A method of synthesizing D-psicose through whole-cell conversion, which comprises:

providing D-fructose as a substrate, and adding the recombinant *B. licheniformis* of claim 1 or a whole-cell catalyst comprising the recombinant *B. licheniformis* to the substrate, and incubating at 50 °C to 70 °C for 5 to 10 hours.

6. The method according to claim 5, which further comprises:

isolating the recombinant *B. licheniformis* or the whole-cell catalyst after incubating by centrifugation or filtration, and adding the recovered *B. licheniformis* or the whole-cell catalyst to a reaction system comprising the D-fructose to synthesize additional D-psicose.

* * * * *